(12) United States Patent
Giles et al.

(10) Patent No.: US 7,091,359 B2
(45) Date of Patent: Aug. 15, 2006

(54) PROCESS FOR THE PREPARATION OF THIAZOLIDINEDIONE DERIVATIVES

(75) Inventors: Robert Gordon Giles, Tonbridge (GB); Norman John Lewis, Tunbridge Wells (GB); John Kirby Quick, Crowborough (GB)

(73) Assignee: SmithKline Beecham plc, Brentford (GB)

( * ) Notice: Subject to any disclaimer, the term of this patent is extended or adjusted under 35 U.S.C. 154(b) by 14 days.

(21) Appl. No.: 10/288,072

(22) Filed: Nov. 4, 2002

(65) Prior Publication Data

US 2003/0092742 A1 May 15, 2003

Related U.S. Application Data

(63) Continuation of application No. 10/082,995, filed on Feb. 26, 2002, now abandoned, which is a continuation of application No. 09/530,888, filed as application No. PCT/EP98/06997 on Oct. 17, 1998, now abandoned.

(30) Foreign Application Priority Data

Nov. 4, 1997 (GB) .............................. 9723295

(51) Int. Cl.
C07D 277/04 (2006.01)

(52) U.S. Cl. ..................................... 548/183
(58) Field of Classification Search ................. 548/183
See application file for complete search history.

(56) References Cited

U.S. PATENT DOCUMENTS

| 4,725,610 | A |   | 2/1988 | Meguro et al. ............ 514/369 |
|---|---|---|---|---|
| 5,002,953 | A |   | 3/1991 | Hindley |
| 5,194,443 | A |   | 3/1993 | Hindley |
| 5,232,925 | A |   | 8/1993 | Hindley |
| 5,260,445 | A |   | 11/1993 | Hindley |
| 5,521,201 | A |   | 5/1996 | Hindley et al. |
| 5,646,169 | A | * | 7/1997 | Hindley ...................... 514/369 |
| 5,726,055 | A |   | 3/1998 | Hindley et al. |
| 5,741,803 | A |   | 4/1998 | Pool et al. |
| 5,756,525 | A |   | 5/1998 | Hindley et al. |
| 5,910,592 | A |   | 6/1999 | Pool et al. |
| 6,288,095 | B1 |   | 9/2001 | Hindley et al. |
| 6,632,947 | B1 |   | 10/2003 | Giles et al. ................. 548/183 |
| 2002/0042519 | A1 |   | 4/2002 | Giles et al. |
| 2002/0049240 | A1 |   | 4/2002 | Hindley et al. |
| 2002/0050563 | A1 |   | 5/2002 | Hindley et al. |
| 2002/0106762 | A1 |   | 8/2002 | Hindley et al. |

FOREIGN PATENT DOCUMENTS

| EP | 0 008 203 | 8/1982 |
|---|---|---|
| EP | 0 257 781 | 7/1987 |
| EP | 0 306 228 | 3/1989 |
| WO | WO 92/07838 | 5/1992 |
| WO | WO 92/07839 | 5/1992 |
| WO | WO 93/10254 | 5/1993 |
| WO | WO 93/13095 | 7/1993 |
| WO | WO 94/05659 | 3/1994 |
| WO | WO 98/37073 | 8/1998 |
| WO | WO 99/23095 | 5/1999 |

OTHER PUBLICATIONS

House, Modern Synthetic Reactions $2^{nd}$ ed., pp. 1–8 1972.*
House, Modern Synthetic Reactions 2nd Ed., pp 1–8 (1972).
U.S. Appl. No. 08/458,033, filed Jun. 1, 1995, Hindley et al.
U.S. Appl. No. 09/952,465, filed Sep. 14, 2001, Hindley et al.
U.S. Appl. No. 09/973,970, filed Oct. 9, 2001, Hindley et al.
U.S. Appl. No. 10/005,686, filed Nov. 8, 2001, Giles et al.
U.S. Appl. No. 10/071,824, filed Feb. 7, 2002, Hindley et al.
Teruo et al., "Preparation of Thiazolidine–2,4–Diones as Aldose Reductase Inhibitors". *Chem. Abstracts*, 115(17), Oct. 28, 1991. XP–002066776.

* cited by examiner

*Primary Examiner*—Kamal A. Saeed
(74) *Attorney, Agent, or Firm*—Kathryn L. Sieburth; Stephen Venetianer; Charles M. Kinzig

(57) ABSTRACT

A process for preparing a compound of formula (I) or a tautomeric form thereof or a pharmaceutically acceptable salt thereof, wherein: $A^1$ represents a substituted or unsubstituted aromatic heterocyclyl group; $R^1$ represents a hydrogen atom, an alkyl group, an acyl group, an aralkyl group, wherein the aryl moiety may be substituted or unsubstituted, or a substituted or unsubstituted aryl group; $A^2$ represents a benzene ring having in total up to five substituents; and n represents an integer in the range of from 2 to 6, which process comprises catalytically reducing a compound of formula (II): wherein $A^1$, $R^1$, $A^2$ and n are as defined in relation to formula (I), characterized in that the reduction reaction is carried out using a hydrogen pressure above 20 psi; and thereafter if required forming a pharmaceutically acceptable salt and/or a pharmaceutically acceptable solvate of the compound of formula (I).

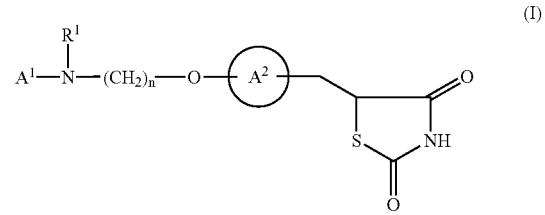

(I)

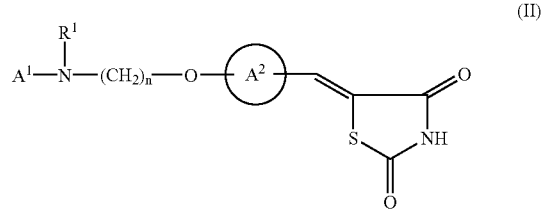

(II)

38 Claims, No Drawings

PROCESS FOR THE PREPARATION OF THIAZOLIDINEDIONE DERIVATIVES

This is a continuation of application Ser. No. 10/082,995 filed Feb. 26, 2002 now abandoned, which is a continuation of Ser. No. 09/530,888 filed Jul. 10, 2000 now abandoned, which is a §371 of PCT/EP98/06997, filed Oct. 17, 1998, which claims priority from GB application No. 9723295.3, filed 04 Nov. 1997.

This invention relates to a novel process and in particular to a process for preparing certain substituted thiazolidinedione derivatives.

European Patent Application, Publication Number 0306228 discloses certain thiazolidinedione derivatives of formula (A):

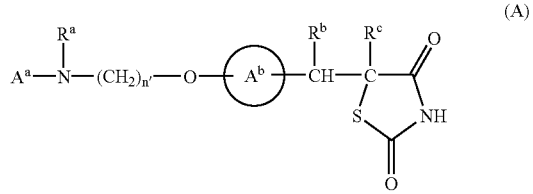

or a tautomeric form thereof or a pharmaceutically acceptable salt thereof, or a pharmaceutically acceptable solvate thereof, wherein:

$A^a$ represents a substituted or unsubstituted aromatic heterocyclyl group;

$R^a$ represents a hydrogen atom, an alkyl group, an acyl group, an aralkyl group, wherein the aryl moiety may be substituted or unsubstituted, or a substituted or unsubstituted aryl group;

$R^b$ and $R^c$ each represent hydrogen or $R^b$ and $R^c$ together represent a bond;

$A^b$ represents a benzene ring having in total up to five substituents; and n' represents an integer in the range of from 2 to 6.

EP 0306228 also discloses a process for reducing the compounds of formula (A) wherein $R^b$ and $R^c$ together represent a bond (the 'benzylidene thiazolidine-2,4-diones') to the corresponding compounds of formula (A) wherein $R^b$ and $R^c$ each represent hydrogen (the 'benzylthiazolidine-2,4-diones'). The particular reduction methods disclosed in EP 0306228 are dissolving metal methods and catalytic hydrogenation methods.

It has now been discovered that when the catalytic hydrogenation of the benzylidene thiazolidine-2,4-diones is carried out using an elevated pressure of hydrogen that the reaction can be effected with a surprising reduction in the catalytic loading and reaction time and, most surprisingly, produces a significant reduction in by-product formation.

Accordingly, the present invention provides a process for preparing a compound of formula (I):

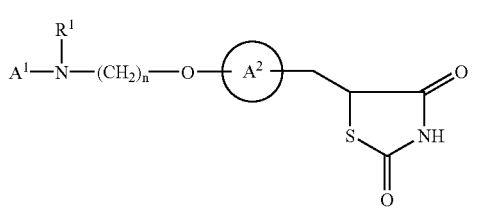

or a tautomeric form thereof or a pharmaceutically acceptable salt thereof, or a pharmaceutically acceptable solvate thereof, wherein:

$A^1$ represents a substituted or unsubstituted aromatic heterocyclyl group;

$R^1$ represents a hydrogen atom, an alkyl group, an acyl group, an aralkyl group, wherein the aryl moiety may be substituted or unsubstituted, or a substituted or unsubstituted aryl group;

$A^2$ represents a benzene ring having in total up to five substituents; and n represents an integer in the range of from 2 to 6, which process comprises catalytically reducing a compound of formula (II):

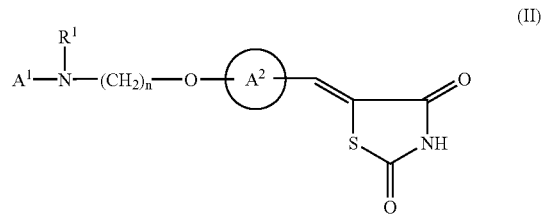

wherein $A^1$, $R^1$, $A^2$ and n are as defined in relation to formula (I), characterised in that the reduction reaction is carried out using a hydrogen pressure above 20 psi, and thereafter, if required, forming a pharmaceutically acceptable salt and/or a pharmaceutically acceptable solvate of the compound of formula (I).

Suitably the reaction is carried out at a pressure in the range of from 50 to 1500 psi, such as 60 to 1500 psi, 75 to 1500 psi, 200 to 1500 psi, 70 to 1000 psi or 200 to 1000 psi, suitably 70 to 1000 psi.

Examples of reaction pressures include 70, 75, 80, 500 and 1000 psi.

A suitable hydrogenation catalyst is a noble metal catalyst, suitably a palladium catalyst.

Favoured catalysts are supported noble metal catalysts, such as a palladium-on-carbon catalyst, typically comprising 5% to 10% of palladium.

A preferred catalyst is a 10% palladium-on-carbon catalyst.

Catalyst loadings (expressed as w/w % of catalyst to substrate) in the reaction are typically in the range of from 5 to 100%, usually 10 to 50% and preferably 25 to 50%.

The reaction may be carried out using any suitable solvent such as acetic acid, or an alkanol, such as methanol or ethanol, preferably admixed with an aqueous mineral acid such as hydrochloric acid; or tetrahydrofuran, preferably admixed with an aqueous mineral acid such as hydrochloric acid. Preferably the solvent is acetic acid or aqueous acetic acid, for example a 4:1 acetic acid:water mixture.

The reaction is carried out at a temperature which provides a suitable rate of formation of the required product, suitably at an elevated temperature, preferably above 70° C., for example in the range of from 80° C. to 115° C.

The compounds of formula (I) are isolated from the reaction and subsequently purified by use of conventional isolation and purification methods such as chromatography and crystallization/recrystalliazation.

The suitable, apt, favoured and preferred values of the variables $A^1$, $A^2$, $R^1$ and n in formulae (I) and (II) are as defined in relation to formula (I) of EP 0306228.

A most preferred value of $A^1$ is a 2-pyridyl group.

A most preferred value of $A^2$ is a moiety of formula:

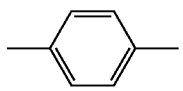

A most preferred value of $R^1$ is a methyl group.

A most preferred value of n is 2.

A most preferred value of formula (I) is 5-{4-[2-(N-methyl-N-(2-pyridyl)amino)ethoxy]benzyl}-2,4-thiazolidinedione, or a tautomeric form thereof or a salt thereof, or a solvate thereof.

Crystalline 5-{4-[2-(N-methyl-N-(2-pyridyl)amino) ethoxy]benzylidene}-2,4-thiazolidinedione is isolated from the present reaction and as such forms a further aspect of the present invention. A suitable crystallization/recrystallization solvent is acetic acid/ denatured ethanol, the crystallization is favourably effected from refluxing solvent which is allowed to cool to provide the required compound.

A most preferred value of formula (II) is 5-{4-[2-(N-methyl-N-(2-pyridyl)amino)ethoxy]benzylidene}-2,4-thiazolidinedione or a tautomeric form thereof or a salt thereof, or a solvate thereof.

Suitable salts are pharmaceutically acceptable salts.

Suitable pharmaceutically acceptable salts include metal salts, such as for example aluminium, alkali metal salts such as sodium or potassium, alkaline earth metal salts such as calcium or magnesium and ammonium or substituted ammonium salts, for example those with lower alkylamines such as triethylamine, hydroxy alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidine, N-benzyl-b-phenethylamine, dehydroabietylamine, N,N'-bisdehydroabietylamine, glucamine, N-methylglucamine or bases of the pyridine type such as pyridine, collidine or quinoline.

In addition should be mentioned those pharmaceutically acceptable salts provided by pharmaceutically acceptable acids including mineral acids, including salts provided by mineral acids, such as hydrobromic, hydrochloric and sulphuric acids, and organic acids, such as methanesulphonic, tartaric and maleic acids, especially tartaric and maleic acid. A preferred salt is a maleate salt.

Suitable solvates are pharmaceutically acceptable solvates, such as hydrates.

The compounds of formula (II) are prepared according to known methods, for example by use of the appropriate method disclosed in EP 0306228. The contents of EP 0306228 are incorporated herein by reference.

The following example illustrates the invention but does not limit it in any way.

EXAMPLE

Reduction of (Z)-5-{4-[2-(N-methyl-N-(2-pyridyl) amino)ethoxy]benzylidene}-2,4-thiazolidinedione to 5-{4-[2-(N-methyl-N-(2-pyridyl)amino)ethoxy] benzyl}-2,4-thiazolidinedione To a solution of (Z)-5-{[4-[2-(N-methyl-N-(2-pyridyl) amino)ethoxy]benzylidene}-2,4-thiazolidinedione (123 kg) in glacial acetic acid (1232 L) is added 10% palladium on charcoal (Johnson-Matthey type 87 L, 123 kg, catalyst contains ~50% w/w water and hence the catalyst loading was 50% w/w). The resulting mixture is hydrogenated at 70–80 p.s.i. hydrogen pressure at about 95° C. After the starting material is consumed (15–20 hours), the reaction mixture is cooled to about 65° C. and the catalyst is removed by filtration. The resulting solution is concentrated under reduced pressure to low volume and the residue is dissolved in denatured ethanol (1000 L) at 60° C. The solution is heated to reflux and then cooled to ambient temperature to effect crystallisation. The product, 5-{[4-[2-(N-methyl-N-(2-pyridyl)amino)ethoxy]benzyl}-2,4-thiazolidinedione, is isolated by filtration, and dried in vacuo at 45° C. Typical yields are 70–80%.

Effect of Change of Reaction Pressure

The above reaction can be performed over a range of pressures resulting in a significant reduction in reaction time and catalyst loading, as shown below.

| Reaction number | Conditions | Reaction Time (hours.) |
|---|---|---|
| 1 | (75 psi, 50% catalyst) | 15–20 |
| 2 | 1000 psi, 50% catalyst | <2 |
| 3 | 1000 psi, 25% catalyst | 7 |
| 4 | 500 psi, 50% catalyst | 4 |
| 5 | 500 psi, 25% catalyst | ca.12 |

What is claimed is:

1. A process for preparing a benzyl thiazolidinedione compound, wherein said benzyl thiazolidinedione compound is selected from the group consisting of 5-{4-[2-(N-methyl-N-(2-pyridyl)amino)ethoxy]benzyl}-2,4-thiazolidinedione, a tautomeric form thereof, a pharmaceutical acceptable salt thereof, and a pharmaceutically acceptable solvate thereof, said process comprising catalytically reducing a benzylidine thiazolidinedione compound, wherein said reduction is conducted using:
a) a hydrogen pressure above 20psi, and
b) a reaction solvent selected from the group consisting of acetic acid, aqueous acetic acid, an alkanol, an alkanol mixed with an aqueous mineral acid, tetrahydrofuran, and tetrahydrofuran admixed with an aqueous mineral acid, wherein said benzylidine thiazolinedione compound is selected from the group consisting of 5-{4-[2-(N-methyl-N-(2-pyridyl)amino)ethoxy]benzylidene}-2,4 -thiazolidinedione, a tautomeric form thereof, a salt thereof, and a solvate thereof.

2. The process according to claim 1, wherein the benzyl thiazolidione compound is the pharmaceutically acceptable acid salt of 5-{4-[2-(N-methyl-N-(2-pyridyl)amino)ethoxy] benzyl{-2,4-thiazolidinedione, a tautomeric form thereof.

3. The process according to claim 2, wherein the pharmaceutically acceptable acid is selected from the group consisting of hydrobromic acid, hydrochloric acid, sulphuric acid, methanesulphonic acid, tartaric acid and maleic acid.

4. The process according to claim 2, wherein the pharmaceutically acceptable acid is maleic acid.

5. The process according to claim 1, wherein the hydrogen pressure is in the range of from 50 to 1500 psi.

6. The process according to claim 1, wherein the hydrogen pressure is in the range of from 70 to 1000 psi.

7. The process according to claim 1, wherein the hydrogen pressure is in the range of from 70 to 80 psi.

8. The process according the claim 1, wherein the catalyst is a palladium catalyst.

9. The process according to claim 8, wherein the catalyst is a palladium-on-carbon catalyst.

10. The process according to claim 9, wherein the palladium-on-carbon catalyst comprises 5% to 10% palladium.

11. The process according to claim 1, wherein the catalyst is a 10% palladium-on-carbon catalyst.

12. The process according to claim 1, wherein the reaction solvent is acetic acid or aqueous acetic acid.

13. The process according to claim 8, wherein the catalyst loading is 10 w/w % to 50 w/w % of catalyst to substrate.

14. The process according to claim 13, wherein the catalyst loading is 25 w/w % to 50 w/w % of catalyst to substrate.

15. The process according to claim 1, wherein the reduction is conducted at a temperature above 70° C.

16. The process according to claim 1, wherein the reduction is conducted at a temperature in the range of from 80° to 115° C.

17. The process according to claim 1, wherein the benzylidine thiazolidinedione compound is selected from the group consisting of 5-{4-[2-N-methyl-N-(2-pyridyl)amino)ethoxy]benzylidene}-2,4-thiazolidinedione, and a tautomeric form thereof.

18. The process according to claim 1, wherein the benzylidine thiazolidinedione compound is selected from the group consisting of a pharmaceutical acceptable salt of 5-{4-[2-(N-methyl-N-(2-pyridyl)amino)ethoxy]benzylidine-2,4-thiazolidinedione and a tautomeric form thereof.

19. The process according to claim 18, wherein the salt is a mineral acid salt.

20. The process according to claim 19, wherein the mineral acid is selected from the group consisting of hydrobromic acid, hydrochloric acid, and sulphuric acid.

21. The process according to claim 18, wherein the salt is an organic acid salt.

22. The process according to claim 21, wherein the organic acid is selected from the group consisting of methanesulphonic acid and tartaric acid.

23. A process for preparing a benzyl thiazolidinedione compound, wherein said benzyl thiazolidinedione compound is selected from the group consisting of 5-{4-[2-(N-methyl-N-(2-pyridyl)amino)ethoxy]benzyl}-2,4-thiazolidinedione, a tautomeric form thereof, a pharmaceutically acceptable salt thereof, and a pharmaceutically acceptable solvate thereof, said process comprising catalytically reducing a benzylidine thiazolidinedione compound, wherein said reduction is conducted using:
a) a 5–10% palladium catalyst,
b) a hydrogen pressure in the range of from 70 to 1000 psi,
c) a reaction solvent selected from the group consisting of acetic acid, aqueous acetic acid, an alkanol, an alkanol mixed with an aqueous mineral acid, tetrahydrofuran, and tetrahydrofuran admixed with an aqueous mineral acid, wherein said benzylidine compound is selected from the group consisting of 5-{4-[2-(N-methyl-N-(2-pyridyl)amino)ethoxyl]benzylidene}-2,4-thiazolidinedione, and a tautomeric form thereof, and a salt thereof, and a solvate thereof.

24. The process according to claim 23, wherein the benzyl thiazolidinedione compound is the pharmaceutically acceptable acid salt of 5-{4-[2-(N-methyl-N-(2-pyridyl)amino)ethoxy]benzyl}-2,4-thiazolidinedione, a tautomeric form thereof, wherein the pharmaceutically acceptable acid is selected from the group consisting of hydrobromic acid, hydrochloric acid, sulphuric acid, methanesulphonic acid, tartaric acid and maleic acid.

25. The process according to claim 24, wherein the pharmaceutically acceptable acid is maleic acid.

26. The process according to claim 23, wherein the reaction solvent is acetic acid or aqueous acetic acid.

27. The process according to claim 23, wherein the hydrogen pressure is in the range of 70 to 80 psi.

28. The process according to claim 23, wherein the reduction conducted at a temperature in the range of from 80° to 115° C.

29. The process according to claim 23, wherein the catalyst is a palladium-on-carbon catalyst comprising 5% to 10% palladium and the catalyst loading is 10 to 50 wt/wt%.

30. The process according to claim 29, wherein the catalyst loading is 25 to 50 wt/wt %.

31. The process according to claim 29, wherein the catalyst is a 10% palladium-on-carbon catalyst.

32. The process according to claim 23, wherein the reaction solvent is acetic acid or aqueous acetic acid.

33. The process according to claim 23, wherin the reduction is conducted at a temperature in the range of from 80° to 115° C.

34. A process for preparing a thiazolidinedione compound, wherein said thiazolidinedione compound is selected from the group consisting of 5-{4-[2-(N-methyl-N-(2-pyridyl)amino)ethoxy]benzyl}-2,4-thiazolidinedione, and a tautomeric form thereof, and a pharmaceutically acceptable salt thereof and a pharmaceutically acceptable solvate thereof, said process comprising catalytically reducing a benzylidine compound, wherein said reduction is conducted:
a) at a temperature in the range of from 80° to 115° C.,
b) at a hydrogen pressure is the range of from 70 to 1000 psi,
c) in the pressure of a 5% to 10% palladium-on-carbon catalyst with a catalyst loading of 25 to 50 wt/wt %,
d) in a reaction solvent selected from the group consisting of acetic acid and aqueous acetic acid, wherein said benzylidine compound is selected from the group consisting of 5-{4-[2-(N-methyl-N-(2-pyridyl)amino)ethoxy]benzylidene}-2,4-thiazolidinedione, a tautomeric form thereof, a salt thereof, a solvate thereof.

35. The process according to claim 34, wherein the benzyl thiasolidinedione compound is the pharmaceutically acceptable acid salt of 5-{4-[2-(N-methyl-N-(2-pyridyl)amino)ethoxy]benzyl}-2,4-thiazolidinedione, a tautomeric form thereof, wherein the pharmaceutically acceptable acid is selected from the group consisting of hydrobromic acid, hydrochloric acid, sulphuric acid, methanesulphonic acid, tartaric acid and maleic acid.

36. The process according to claim 35, wherein the pharmaceutically acceptable acid is maleic acid.

37. The process according to claim 34, wherein the hydrogen pressure is from 70 to 80 psi.

38. The process according to claim 34, wherein the catalyst is a 10% palladium-on-carbon catalyst.

* * * * *

UNITED STATES PATENT AND TRADEMARK OFFICE
CERTIFICATE OF CORRECTION

PATENT NO.        : 7,091,359 B2                                              Page 1 of 1
APPLICATION NO. : 10/288072
DATED             : August 15, 2006
INVENTOR(S)       : Robert Gordon Giles, Norman John Lewis and John Kirby Quick It is certified that error appears in the above-identified patent and that said Letters Patent is hereby corrected as shown below:

Cover Page: (63) Related U.S. Application Data
Continuation of Application No. 10/082,995, filed Feb. 26, 2002, now abandoned, which is a continuation of Application No. 09/530,888, filed as Application No. PCT/EP98/06997, on October 27, 1998, now abandoned.

Specification: Column 1, Line 7:
which is a §371 of PCT/EP98/06997, filed Oct. 27, 1998, ...

Signed and Sealed this

Tenth Day of April, 2007

JON W. DUDAS
*Director of the United States Patent and Trademark Office*